(12) United States Patent
Wang et al.

(10) Patent No.: US 7,887,883 B2
(45) Date of Patent: *Feb. 15, 2011

(54) COMPOSITION AND METHOD FOR LOW TEMPERATURE DEPOSITION OF SILICON-CONTAINING FILMS

(75) Inventors: Ziyun Wang, Bethel, CT (US); Chongying Xu, New Milford, CT (US); Thomas H. Baum, New Fairfield, CT (US); Bryan C. Hendrix, Danbury, CT (US); Jeffrey F. Roeder, Brookfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/777,519

(22) Filed: May 11, 2010

(65) Prior Publication Data

US 2010/0221914 A1 Sep. 2, 2010

Related U.S. Application Data

(63) Continuation of application No. 12/247,120, filed on Oct. 7, 2008, now Pat. No. 7,713,346, which is a continuation of application No. 10/699,079, filed on Oct. 31, 2003, now Pat. No. 7,446,217, which is a continuation-in-part of application No. 10/294,431, filed on Nov. 14, 2002, now Pat. No. 7,531,679.

(51) Int. Cl.
*C23C 16/30* (2006.01)
*C23C 16/34* (2006.01)
*C23C 16/40* (2006.01)
*C07F 7/02* (2006.01)

(52) U.S. Cl. ............... 427/248.1; 427/58; 106/287.11; 556/410

(58) Field of Classification Search ............ 106/287.11; 556/410; 427/58, 248.1
See application file for complete search history.

(56) References Cited

U.S. PATENT DOCUMENTS

| | | | |
|---|---|---|---|
| 5,204,141 A | 4/1993 | Roberts et al. | |
| 5,424,095 A | 6/1995 | Clark et al. | |
| 5,578,530 A | 11/1996 | Muroyama et al. | |
| 5,744,196 A | 4/1998 | Laxman et al. | |
| 6,013,235 A | 1/2000 | Brinson et al. | |
| 6,383,955 B1 | 5/2002 | Matsuki et al. | |
| 6,410,463 B1 | 6/2002 | Matsuki | |
| 6,936,548 B2 * | 8/2005 | Dussarrat et al. | 438/769 |
| 7,019,159 B2 * | 3/2006 | Dussarrat et al. | 556/410 |
| 7,064,083 B2 * | 6/2006 | Dussarrat et al. | 438/769 |
| 7,132,723 B2 | 11/2006 | Park et al. | |
| 7,446,217 B2 * | 11/2008 | Wang et al. | 556/410 |
| 7,531,679 B2 | 5/2009 | Wang et al. | |
| 2004/0146644 A1 | 7/2004 | Xiao et al. | |
| 2005/0080285 A1 | 4/2005 | Wang et al. | |
| 2005/0080286 A1 | 4/2005 | Wang et al. | |
| 2008/0160174 A1 | 7/2008 | Wang et al. | |
| 2009/0084288 A1 | 4/2009 | Wang et al. | |

FOREIGN PATENT DOCUMENTS

| | | | |
|---|---|---|---|
| EP | 1 441 042 A1 | | 7/2004 |
| EP | 1 149 934 B1 | | 8/2005 |
| JP | 08-022986 | * | 1/1996 |
| JP | 2000-080476 A | | 3/2000 |
| WO | 03046253 A1 | | 6/2003 |

OTHER PUBLICATIONS

Wan et al, "Synthesis of (Dialkylamino)disilanes", Inorg. Chem. (1993), pp. 341-344.*
Sergeeva, et al., "Chem. Abstract 1960:127948; Abstract of 'Synthesis of alkyl- and dialkylbis(1,1-dialkylhydrazino)silanes'", "Zhurnal Obshceii Khimii", 1960, pp. 694-695, vol. 30 (Abstract Only).
Sergeeva, et al., "Synthesis of 1,1-dialkyl-2-(trialkylsilyl)hydrazines (CAPLUS Abstract)", "Khim. i Prakt. Primenenie Kremneorg. Soedinenii", 1958, pp. 235-241, No. 1 (Abstract Only).
Chen, L.C., et al., "Crystalline silicon carbon nitride: A wide band gap semiconductor", "Appl. Phys. Letters.", May 11, 1998, pp. 2463-2465, vol. 72, No. 19.
Wikipedia Entry for the term 'Vapor Pressure', "Found online at http://en.wikipedia.org/wiki/Vapor_pressure", Jul. 17, 2007.
Denk, Michael, et al., "Synthesis and Structure of a Stable Silylene", "J. Am. Chem. Soc.", Mar. 23, 1994, pp. 2691-2692, vol. 116, No. 6.
Gibson, George, et al., "The Reaction of Silicon Tetrachloride with N,N-Dimethylhydrazine and Hydrazine", "Inorg. Chem.", Aug. 1963, pp. 876-878, vol. 2, No. 4.
Heinicke, Joachim, et al., "Aminosubstituted disilanes: Synthesis by unsymmetrical and symmetrical reductive coupling", "Heteroatom Chem.", 1998, pp. 311-316, vol. 9, No. 3.
Huppmann, Frank, et al., "English Abstract: Reaktionen subvalenter Verbindungen des Siliciums mit alkylierten Aromaten", "Journal of Organometallic Chemistry", 1994, pp. 217-228, vol. 483.
Kito, Hideyoshi, "Chem Abstract 1996:212092; Manufacture of Silicon nitride-based electrically insulating film by plasma CVD", "Chemical Abstracts", 1996.
Lee, Gyun-Hwan, et al., "Bis[bis(trimethylsilyl)amino]silylene, an Unstable Divalent Silicon Compound", Jul. 9, 2003, pp. 8114-8115, vol. 125, No. 27.

(Continued)

*Primary Examiner*—David M Brunsman
(74) *Attorney, Agent, or Firm*—Steven J. Hultquist; Intellectual Property/Technology Law; Margaret Chappuis

(57) ABSTRACT

This invention relates to silicon precursor compositions for forming silicon-containing films by low temperature (e.g., <300° C.) chemical vapor deposition processes for fabrication of ULSI devices and device structures. Such silicon precursor compositions comprise at least one disilane derivative compound that is fully substituted with alkylamino and/or dialkylamino functional groups.

8 Claims, 2 Drawing Sheets

OTHER PUBLICATIONS

Mitzel, Morbert W., "Simple silylhydrazines as models for Si-N beta-donor interactions in SiNN units", "Chem. Eur. J.", 1998, pp. 692-698, vol. 4, No. 4.

Scherer, Otto, et al., "Ethylenimine and imidazolidinone derivatives of silicon", "Chem. Abstracts", 1965.

Schuh, et al., "Disilanyl-Amines-Compounds Comprising the Structural Unit Si-Si-N, as Single Source Precursors for Plasma-Enhanced . . . ", 1993, pp. 1347-1352, vol. 619.

Witte-Abel, Henning, et al., "Kondensationen von Silylhydrazinen und Estern zu Silylhydrazonen und Pyrazolnen", "J. Organometallic Chem.", Aug. 15, 1999, pp. 341-347, vol. 585, No. 2 (Only English Abstract Available).

Sergeeva, Z.I., et al., "A new method of synthesis of organosilicon hydrazines (Chem. Abstracts Acession No. 1963:27415)", "Zhurnal Obshchei Khimii", 1962, pp. 1987-1993, vol. 32 )(Abstract Only).

Sergeeva, Z. I., et al., "Reaction of nonsymmetric dialkylhydrazines with alkylchloro-silanes (Caplus Abstract 1963:455161)", "Zhurnal Obshchei Khimii", 1963, pp. 1874-1878, vol. 33, No. 6.

Smirnova, T.P., et al., "Plasma-enhanced chemical vapor deposition of silicon carbonitride films from volatile silyl derivatives of . . . ", "Proceedings of the 3rd Symposium on Theoretical and Applied Plasma Chemistry, High Energy Chemistry", 2003, pp. 303-309, vol. 37, No. 5.

Smirnova, T.P., et al., "SiCN alloys obtained by remote plasma chemical vapour deposition from novel precursors", "Thin Solid Films", Apr. 1, 2003, pp. 144-151, vol. 429, No. 1-2.

Soldner, Marcus, et al., "1,2-Disilanediyl Bis(triflate), F3CSO3-SiH2SiH2-O3SCF3, as the Key Intermediate for a Facile Preparation of Open-Chain . . . ", "Inorg. Chem.", Apr. 23, 1997, pp. 1758-1763, vol. 36, No. 9.

Yang, Jinchao, et al., "Synthesis of 1,4-disilacyclohexa-2,5-dienes", "Journal of Organometallic Chemistry", 2002, pp. 276-288, vol. 649.

Yang, Jinchao, et al., "Disilane-Catalyzed and Thermally Induced Oligomerizations of Alkynes: A Comparison", "Organometallics", Mar. 6, 2000, pp. 893-900, vol. 19, No. 5.

Voronkov, et al., "Izvestiya Vysshikh Uchebnykh Zavedenii", "Materialy Elektronnoi Tekhniki", 2002, pp. 5760, vol. 4 (Only English Abstract Provided).

Wannagat, U. et al., "Chem. Abstracts Accession No. 1959:93473—abstract of 'Hydrazine-silicon compounds II Mixed alkyl-or aryl-substituted hydrazines'", "Z. anorg. u allgem. Chem.", 1959, pp. 341-348, vol. 299.

Wannagat, U., et al., "Chem Abstract Accession No. 1966:104351; 'Si-N compounds. L-III. Si-N2H4 compounds. 7. Some new hyrdazinosilanes'", "Monatshefte fuer Chemie", 1965, pp. 1902-1908, vol. 96, No. 6.

Wannagat, U., et al., "Chem Abstract Accession No. 1966:18737; Silicon-Nitrogen compounds. LXI. Silicaon-hydrazine compounds. 11. Hypergolity of silyhydrazi", "Monatshefte fuer Chemie", 1966, pp. 1157-1162, vol. 97, No. 4.

West, Robert, et al., "Tetramesityldisilene, a Stable Compound Containing a Silicon-Silicon Double Bond", "Science", Dec. 18, 1981, pp. 1343-1344, vol. 214, No. 4527.

West, Robert, et al., "Stable silylenes: Synthesis, structure, reactions", "Pure & Appl. Chem.", 1996, pp. 785-788, vol. 68, No. 4.

West, Robert, et al., "Chemical Shift Tensors and NICS Calculations for Stable Silylenes", "J. Am. Chem. Soc.", Feb. 25, 1998, pp. 1639-1640, vol. 120, No. 7.

Co-pending U.S. Appl. No. 12/578,262, published as US 2010/0068894 Mar. 2010.

Co-pending U.S. Appl. No. 12/862,739, filed Aug. 24, 2010.

* cited by examiner

COMPOSITION AND METHOD FOR LOW TEMPERATURE DEPOSITION OF SILICON-CONTAINING FILMS

This application is a continuation under 35 USC 120 of U.S. patent application Ser. No. 12/247,120 filed Oct. 7, 2008 (now U.S. Pat. No. 7,713,346 issued May 11, 2010), which is a continuation under 35 USC 120 of U.S. patent application Ser. No. 10/699,079 filed Oct. 31, 2003 (now U.S. Pat. No. 7,446,217 issued Nov. 4, 2008), which is a continuation-in-part under 35 USC 120 of U.S. patent application Ser. No. 10/294,431, filed Nov. 14, 2002 (now U.S. Pat. No. 7,531,679 issued May 12, 2009). The disclosures of each of the aforementioned patent applications are hereby incorporated herein by reference, in their respective entireties, for all purposes.

FIELD OF THE INVENTION

The present invention relates generally to the formation of silicon-containing films in the manufacture of semiconductor devices, and more specifically to compositions and methods for forming such films, e.g., films comprising silicon, silicon nitride ($Si_3N_4$), siliconoxynitride ($SiO_xN_y$), silicon dioxide ($SiO_2$), etc., low dielectric constant (k) thin silicon-containing films, high k gate silicate films and low temperature silicon epitaxial films.

DESCRIPTION OF THE RELATED ART

Silicon nitride ($Si_3N_4$) thin films are widely employed in the microelectronic industry as diffusion barriers, etch-stop layers, sidewall spacers, etc.

Deposition of silicon nitride films by chemical vapor deposition (CVD) techniques is a highly attractive methodology for forming such films. CVD precursors currently used include bis(tert-butylamino)silane (BTBAS) or silane/ammonia, but such precursors usually require deposition temperature higher than 600° C. for forming high quality $Si_3N_4$ films, which is incompatible with the next generation IC device manufacturing, where deposition temperature of below 500° C., and preferably about 450° C., is desired. Therefore, development of low-temperature silicon-containing CVD precursors is particularly desired.

Presently, hexachlorodisilane, $Cl_3Si$—$SiCl_3$, is being studied as a candidate precursor for low-temperature CVD formation of silicon nitride upon reaction with ammonia gas. The drawbacks of using hexachlorodisilane in CVD processes include: (i) formation of large amount of $NH_4Cl$ during the process, which leads to the particle contamination and solid build-up in vacuum system and exhaust lines; (ii) possible chlorine incorporation in the chips, which could significantly reduce their life time and long-term performance. It is therefore desirable to develop new chlorine-free precursors that can be used for low-temperature CVD formation of silicon nitride.

SUMMARY OF THE INVENTION

The present invention relates generally to the formation of silicon-containing films, such as films comprising silicon, silicon nitride ($Si_3N_4$), siliconoxynitride ($SiO_xN_y$), silicon dioxide ($SiO_2$), etc., silicon-containing low k films, high k gate silicates, and silicon epitaxial films, among which silicon nitride thin films are preferred, in the manufacture of semiconductor devices, and more specifically to compositions and methods for forming such silicon-containing films.

The present invention in one aspect relates to a group of chlorine-free disilane derivatives that are fully substituted with alkylamino and/or dialkylamino functional groups and can be used as CVD precursors for deposition of silicon-containing thin films.

Such disilane derivative compounds can be represented by the general formula of:

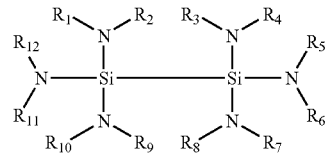

wherein $R_1$-$R_{12}$ may be the same as or different from one another and each is independently selected from the group consisting of H, $C_1$-$C_5$ alkyl, and $C_3$-$C_6$ cycloalkyl.

Preferably, the disilane derivative compound of the present invention is characterized by a symmetrical structure in relation to the Si—Si bond. In one preferred embodiment of the present invention, such disilane derivative compound contains at least two alkylamino functional groups that are symmetrically distributed in relation to the Si—Si bond. Such disilane derivative compound may also contain two or more dialkylamino functional groups symmetrically distributed in relation to the Si—Si bond.

More preferably, such disilane derivative compound is selected from the group consisting of $(NEt_2)_2(HNMe)Si$—$Si(HNMe)(NEt_2)_2$, $(HNBu^t)_2(HNMe)Si$—$Si(HNMe)(HNBu^t)_2$, and $(HNBu^t)_2(NH_2)Si$—$Si(NH_2)(HNBu^t)_2$, wherein Et is used as the abbreviation of ethyl, $Bu^t$ is used as the abbreviation of t-butyl, and Me is used as the abbreviation of methyl, consistently throughout herein.

Another aspect of the present invention relates to a method for forming a silicon-containing film on a substrate, comprising contacting a substrate under chemical vapor deposition conditions including a deposition temperature of below 550° C., preferably about 500° C., with a vapor of a disilane compound that is fully substituted with alkylamino and/or dialkylamino functional groups.

Still another aspect of the present invention relates to a method of making $(NEt_2)_2(HNMe)Si$—$Si(HNMe)(NEt_2)_2$, by reacting $(NEt_2)_2(Cl)Si$—$Si(Cl)(NEt_2)_2$ with excess $H_2NMe$.

Yet a further aspect of the present invention relates to a method of making $(HNBu^t)_2(HNMe)Si$—$Si(HNMe)(HNBu^t)_2$, by reacting $(HNBu^t)_2(Cl)Si$—$Si(Cl)(HNBu^t)_2$ with $LiN(H)Me$.

A still further aspect of the present invention relates to a method of making $(HNBu^t)_2(NH_2)Si$—$Si(NH_2)(HNBu^t)_2$, by reacting $(HNBu^t)_2(Cl)Si$—$Si(Cl)(HNBu^t)_2$ with $LiNH_2$.

A still further aspect of the present invention relates to a method of forming silicon-containing thin films on a substrate, by contacting the substrate under chemical vapor deposition conditions with a vapor of an above-described disilane derivative compound, or a mixture of two or more above-described disilane derivatives. Preferably, the deposition temperature is not higher than 550° C., more preferably not higher than 500° C., and most preferably not higher than 450° C.

Other aspects, features and embodiments of the invention will be more fully apparent from the ensuing disclosure and appended claims.

DETAILED DESCRIPTION OF THE INVENTION AND PREFERRED EMBODIMENTS THEREOF

The present invention relates to silicon precursors for CVD formation of films on substrates, such as silicon precursors for forming low k dielectric films, high k gate silicates, low temperature silicon epitaxial films, and films comprising silicon, silicon oxide, silicon oxynitride, silicon nitride, etc., as well as to corresponding processes for forming such films with such precursors.

Disilane derivatives that are fully substituted with alkylamino and/or dialkylamino functional groups, free of any halogen-substitutes, are found particularly suitable for low-temperature deposition of silicon nitride thin films.

Such fully substituted disilane compound may be represented by the generic formula of:

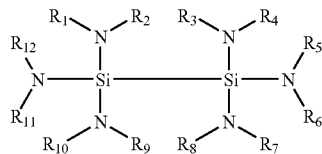

wherein $R_1$-$R_{12}$ may be the same as or different from one another and each is independently selected from the group consisting of H, $C_1$-$C_5$ alkyl, and $C_3$-$C_6$ cycloalkyl.

The fully substituted disilane compounds of the above formula are advantageously characterized by a melting temperature of less than 100° C., and a vaporization temperature of less than 300° C. Moreover, such disilane compounds can be transported in vapor form at less than 300° C., with no or little (≦1%) residual material at atmospheric pressure. The silicon-containing films that can be formed using such disilane precursor compounds include low dielectric constant (k) thin films, high k gate silicates and silicon epitaxial films. In a particularly preferred embodiment of the invention, the films formed using such disilane precursors comprise silicon nitride.

Preferred disilane compounds of the above-described formula include those characterized by a symmetrical structure in relation to the Si—Si bond, such as $(NEt_2)_2(HNMe)Si—Si(HNMe)(NEt_2)_2$, $(HNBu^r)_2(HNMe)Si—Si(HNMe)(HNBu^r)_2$, and $(HNBu^r)_2(NH_2)Si—Si(NH_2)(HNBu^r)_2$, etc. More preferably, such disilane compounds contain at least two alkylamino functional groups and/or two or more dialkylamino functional groups that are symmetrically distributed in relation to the Si—Si bond. For example, both $(HNBu^r)_2(HNMe)Si—Si(HNMe)(HNBu^r)_2$ and $(HNBu^r)_2(NH_2)Si—Si(NH_2)(HNBu^r)_2$ contain four t-butylamino functional groups that are symmetrically distributed in relation to the Si—Si bond; $(NEt_2)_2(HNMe)Si—Si(HNMe)(NEt_2)_2$ contains two methylamino functional groups and four diethylamino functional groups that are symmetrically distributed in relation to the Si—Si bond.

Figure 1:
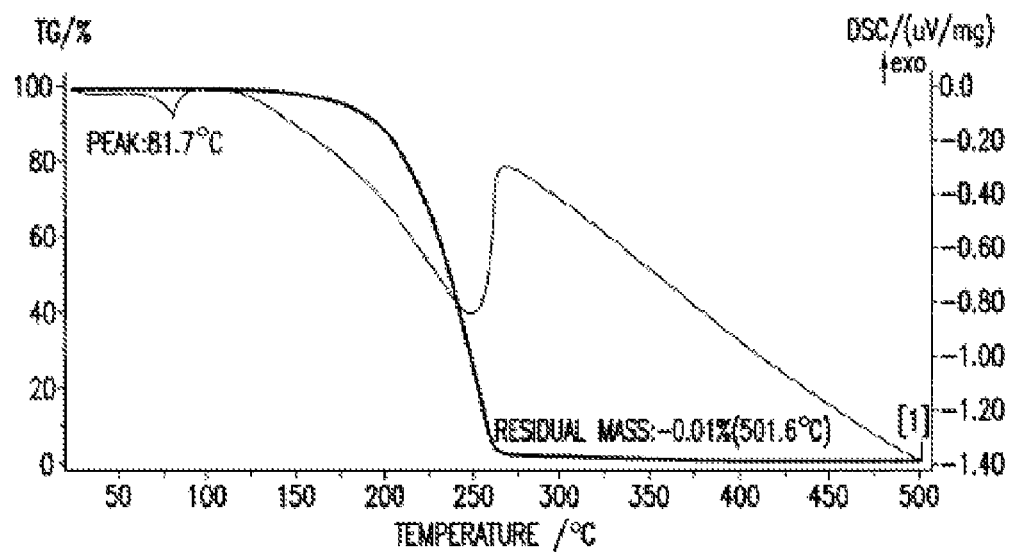
FIG. 1 is a STA plot for $(NEt_2)_2(HNMe)Si$—$Si(HNMe)(NEt_2)_2$.

FIG. 1 shows the STA plot for $(NEt_2)_2(HNMe)Si—Si(HNMe)(NEt_2)_2$, which has a melting temperature of about 81.7° C., and can be transported in its vapor form completely with almost no residual material at about 300° C. at atmospheric pressure or in a flow of inert gas.

Figure 2:
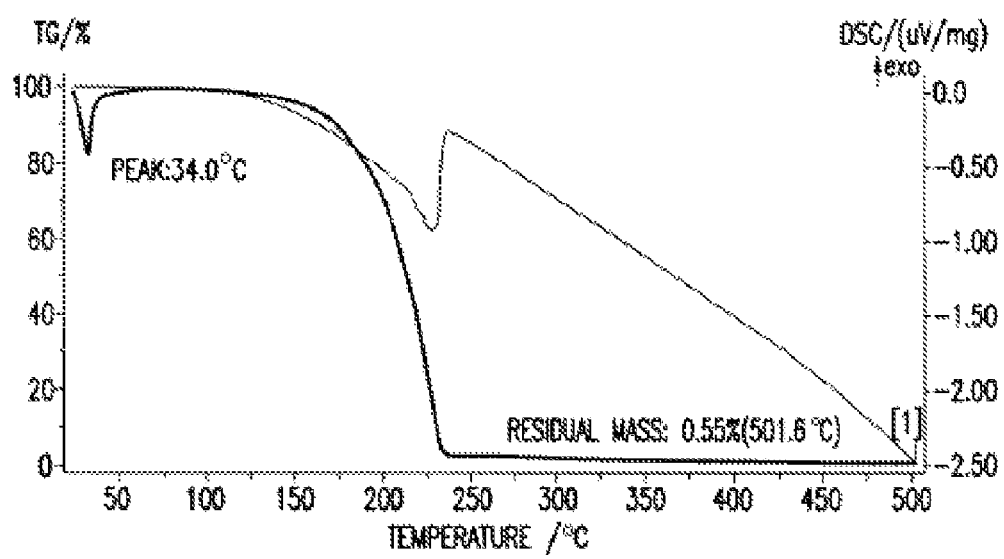
FIG. 2 is a STA plot for $(HNBu^t)_2(HNMe)Si$—$Si(HNMe)(HNBu^t)_2$.

FIG. 2 is the STA plot for $(HNBu^r)_2(HNMe)Si—Si(HNMe)(HNBu^r)_2$, showing an even lower melting temperature of about 34.0° C., with only 0.55% residual material when vaporized at about 250° C. at atmospheric pressure or in a flow of inert gas.

Figure 3:
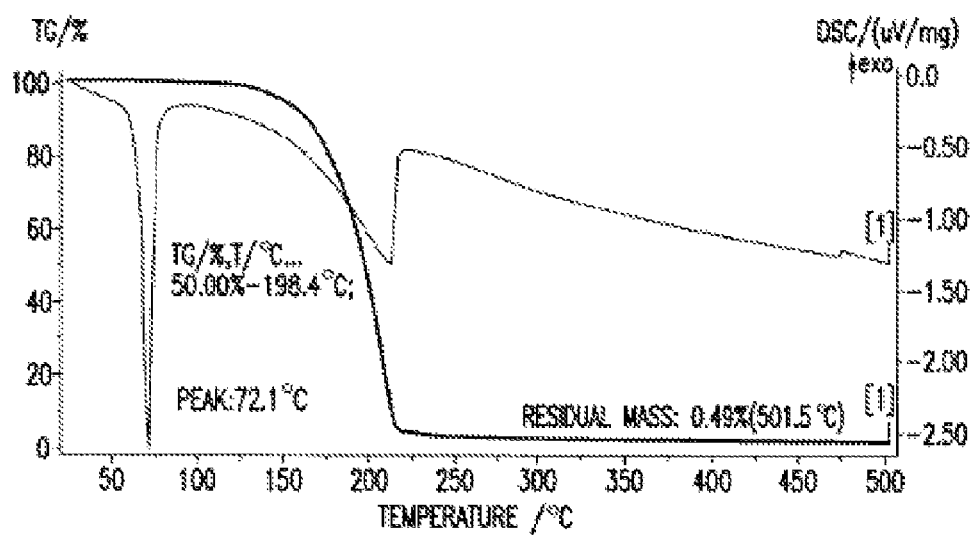
FIG. 3 is a STA plot for $(HNBu^r)_2(NH_2)Si—Si(NH_2)(HNBu^r)_2$.

FIG. 3 is the STA plot for $(HNBu^r)_2(NH_2)Si—Si(NH_2)(HNBu^r)_2$, which has a melting temperature of about 72.1° C. and can be transported in its vapor form at about 250° C., with only 0.49% residual material noted at 500° C.

Figure 4:
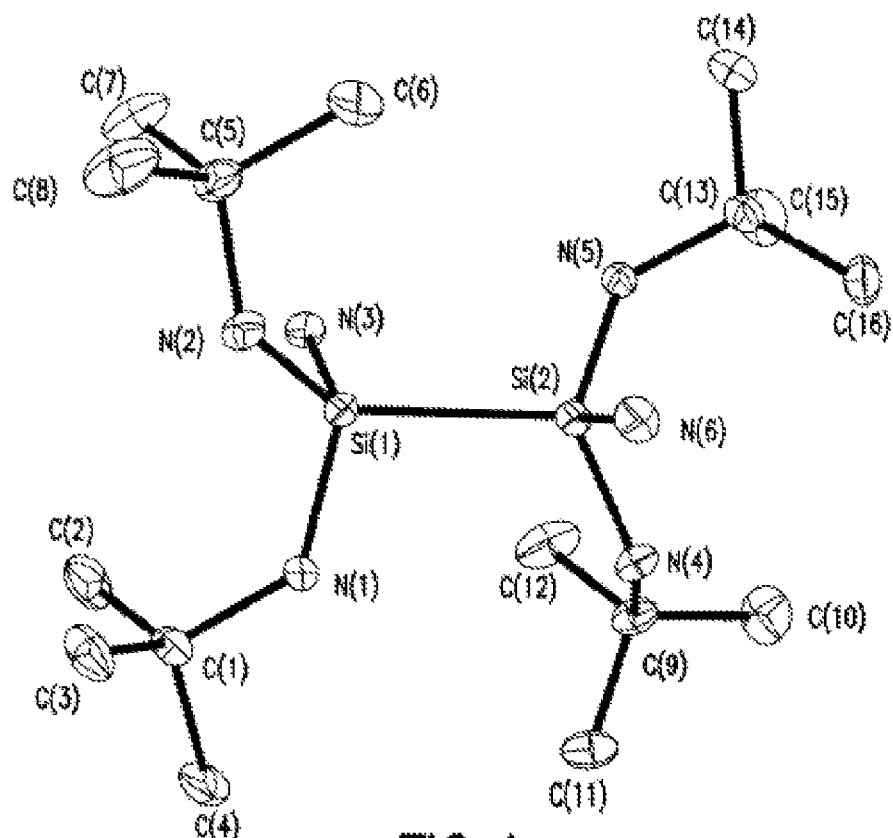
FIG. 4 is an X-ray crystal structure of the compound $(HNBu^r)_2(NH_2)Si—Si(NH_2)(HNBu^r)_2$.

FIG. 4 further shows an X-ray crystal structure of the disilane derivative compound $(HNBu^r)_2(NH_2)Si—Si(NH_2)(HNBu^r)_2$.

Synthesis of several preferred disilane derivatives is described in the following examples:

Example 1

Synthesis of $(NEt_2)_2(HNMe)Si—Si(HNMe)(NEt_2)_2$

The disilane compound $(NEt_2)_2(HNMe)Si—Si(HNMe)(NEt_2)_2$ can be synthesized by reacting $(NEt_2)_2(Cl)Si—Si(Cl)(NEt_2)_2$ with excess amount of $H_2NMe$, according to the following equations:

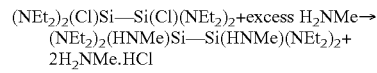

Specifically, a 1 L flask was filled with a solution comprising 500 mL diethyl ether and 20 grams (48.2 mmol) of $(NEt_2)_2(Cl)Si—Si(Cl)(NEt_2)_2$. $H_2NMe$ was bubbled into such solution. White precipitate was observed during the addition of $H_2NMe$. Approximately 20 grams of $H_2NMe$ (644.25 mmol) was added into the 1 L reaction flask during a ten-hour period. The resulting mixture was filtered, and all volatile materials were removed from the filtrate under vacuum conditions. The crude yield was about 90%. Either vacuum distillation or low temperature crystallization is used to purify the end product. $^1H$ NMR ($C_6D_6$): δ 0.39 (br, 2H), 1.11 (t, 24H), 2.54 (d, 6H), 3.06 (q, 16H). $^{13}C\{^1H\}$ NMR ($C_6D_6$): δ 14.8 (—$CH_2CH_3$), 28.2 (—$CH_2CH_3$), 38.3 (—$HNCH_3$). m/z: 332 [$M^+$-(—$NEt_2$)], 202 [$M^+$-(—Si(HNMe)($NEt_2$)$_2$].

Example 2

Synthesis of $(HNBu^r)_2(HNMe)Si—Si(HNMe)(HNBu^r)_2$

The disilane compound $(HNBu^r)_2(HNMe)Si—Si(HNMe)(HNBu^r)_2$ can be synthesized by reacting $(HNBu^r)_2(Cl)Si—Si(Cl)(HNBu^r)_2$ with about 2 molar ratio of LiN(H)Me, according to the following equations:

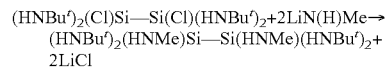

Specifically, a 250 mL flask was charged with a solution comprising 100 mL diethyl ether and 20.1 mL (1.6M, 32.2 mmol) of n-butyllithium hexanes solution. 1 gram of $H_2NMe$ was then bubbled into such solution at 0° C. White precipitate material was formed immediately. Upon completion of this addition, the 250 mL reaction flask was allowed to warm up to room temperature and was stirred for about one hour. Subsequently, 5 grams of $(HNBu^r)_2(Cl)Si—Si(Cl)(HNBu^r)_2$ (12 mmol) in 40 mL diethyl ether was slowly added into the reaction flask, which was stirred overnight and then refluxed for addition four hours. The mixture was filtered at room temperature. 3.5 grams (72% yield) viscous liquid crude product was obtained after removing the volatiles from the filtrate. The end product is purified by recrystallization from hexanes solution at −25° C., and it has a melting temperature between 34° C. and 38° C. $^1H$ NMR ($C_6D_6$): δ 0.38 (br, 2H, H-NMe), 0.99 (br, 4H, H-Nbu$^r$), 1.31 (s, 36H), 2.66 (d, 6H), 3.06 (q, 16H). $^{13}C\{^1H\}$ NMR ($C_6D_6$): δ 28.3 (—$C(CH_3)_4$), 34.2 (—HNCH$_3$), 49.4 (—C(CH$_3$)$_3$). m/z: 332 [M$^+$-(—HNBu$^r$)], 202 [M$^+$-(—Si(HNMe)(HNBu$^r$)$_2$].

Example 3

Synthesis of (HNBu$^r$)$_2$(NH$_2$)Si—Si(NH$_2$)(HNBu$^r$)$_2$

The disilane compound (HNBu$^r$)$_2$(NH$_2$)Si—Si(NH$_2$)(HNBu$^r$)$_2$ can be synthesized by reacting (HNBu$^r$)$_2$(Cl)Si—Si(Cl)(HNBu$^r$)$_2$ with about 2 molar ratio of LiNH$_2$, according to the following equations:

(HNBu$^r$)$_2$(Cl)Si—Si(Cl)(HNBu$^r$)$_2$+2LiNH$_2$→(HNBu$^r$)$_2$(NH$_2$)Si—Si(NH$_2$)(HNBu$^r$)$_2$+2LiCl

Specifically, a 250 mL flask was charged with a solution comprising 100 mL monoglyme and 5 grams (12.0 mmol) of HNBu$^r$)$_2$(Cl)Si—Si(Cl)(HNBu$^r$)$_2$. 0.58 gram (25.2 mmol) LiNH$_2$ was added and heated to reflux for approximately four hours. All volatile material was removed from the resulting mixture under vacuum. Approximately 150 mL hexanes was used to extract the product. After filtration, the filtrate was concentrated to about 80 mL and stored in a freezer overnight. White crystal material was separated from the solution and dried under vacuum, resulting in about 60% yield. About 20% of such dried crystal material was further recovered in purified form through recrystallization. $^1$H NMR (C$_6$D$_6$): δ 0.60 (br, 4H), 1.32 (s, 36H). $^{13}$C{$^1$H} NMR (C$_6$D$_6$): δ 34.2 (—C(CH$_3$)$_4$), 49.6 (—C(CH$_3$)$_3$). m/z: 232 [M$^+$-(—HNBu$^r$)], 188 [M$^+$-(—Si(NH$_2$)(HNBu$^r$)$_2$].

The disilane derivative compounds of the present invention as described hereinabove can be used, either separately or as mixtures, for low-temperature CVD deposition of various silicon-containing films, including silicon nitride thin films, consistent with the disclosure in U.S. patent application Ser. No. 10/294,431 for "Composition and Method for Low Temperature Deposition of Silicon-Containing Films Including Silicon Nitride, Silicon Dioxide and/or Silicon-Oxynitride" filed on Nov. 14, 2002 and issued as U.S. Pat. No. 7,531,679 on May 12, 2009, the content of which is incorporated by reference in its entirety for all purposes.

Preferably, one or more of the above-described disilane derivatives are first dissolved in a hydrocarbon solvent or a solvent system that comprises at least one hydrocarbon solvent. Suitable hydrocarbon solvents for the practice of the present invention include, but are not limited to, alkylamines such as HN$^i$Pr$_2$, wherein $^i$Pr is used herein as the abbreviation of isopropyl. Such solution containing the disilane derivative(s) of the present invention is vaporized at a temperature that is not higher than 300° C., preferably not higher than 150° C., and more preferably about 120° C., and transported to the deposition chamber together with a carrier gas, such as helium or argon, for contact with a heated substrate surface to deposit the silicon-containing thin films.

Silicone nitride deposition processes using one or more disilane derivatives of the present invention are described in the following examples:

Example 4

Silicon Nitride Deposition with (HNEt)$_3$Si—Si(HNEt)$_3$ and HN$^i$Pr$_2$

A solution of the compound (HNEt)$_3$Si—Si(HNEt)$_3$ was prepared at a concentration of 0.4M in a hydrocarbon solvent and at a concentration of 0.036M in HN$^i$Pr$_2$. These solutions were metered at 0.0127 ml/minute and 0.167 ml/minute, respectively into a vaporizer that was held at temperature of 120° C. and had a flow of 10 standard cubic centimeters per minute (sccm) of He as a carrier gas. The vapor was mixed with 50 sccm or 25 sccm, respectively of NH$_3$ in a showerhead vaporizer device that was maintained at 120° C. and thereby dispersed over the surface of a heated Si(100) wafer. The chamber pressure was maintained at 10 Torr to 60 Torr during deposition. The growth rate of the silicon nitride films ranged from 72 Å/minute to 34 Å/minute depending upon pressure, temperature, NH$_3$ rate, and precursor rate.

Chemical analysis of the films, by a combination of RBS (Rutherford Backscattering), HFS (Hydrogen Forward Scattering), and NRA (Nuclear Reaction Analysis), and spectroscopic ellipsometry revealed that (HNEt)$_3$Si—Si(HNEt)$_3$ with HN$^i$Pr$_2$ deposits films with decreased hydrogen impurity and increased carbon impurity for the same ultra-violet absorption edge (UVAE), deposition rate, and index of refraction as shown in Table 1 below.

TABLE 1

Film composition for various deposition conditions using the precursor (HNEt)$_3$Si—Si(HNEt)$_3$ with the nitrogen source and solvent HN$^i$Pr$_2$

| NH$_3$ (sccm) | HN$^i$Pr$_2$ (sccm) | T (° C.) | P (torr) | Rate (Å/min) | n | UVAE (eV) | H (at %) | C (at %) | N/Si |
|---|---|---|---|---|---|---|---|---|---|
| 25 | 25 | 550 | 20 | 41 | 1.92 | 4.13 | 16.5 | 10.8 | 1.23 |
| 50 | 0 | 550 | 60 | 44 | 1.85 | 4.31 | 19.0 | 5.6 | 1.24 |
| 25 | 25 | 550 | 10 | 41 | 1.98 | 3.91 | 14.7 | 11.0 | 1.10 |
| 50 | 0 | 550 | 20 | 36 | 1.94 | 3.82 | 15.0 | 6.9 | 1.12 |

Example 5

Silicon Nitride Deposition with (NEt$_2$)$_2$(HNMe)Si—Si(HNMe)(NEt$_2$)$_2$

A solution of the compound of Example 1, (NEt$_2$)$_2$(HNMe)Si—Si(HNMe)(NEt$_2$)$_2$, was prepared at a concentration of 0.4M in a hydrocarbon solvent. This solution was metered at 0.0127 ml/minute or 0.025 ml/minute into a vaporizer that was held at temperature of 120° C. and had a flow of 10 standard cubic centimeters per minute (sccm) of He as a carrier gas. The vapor was mixed with 50 sccm or 300 sccm of NH$_3$ in a showerhead vaporizer device that was maintained at 120° C. and thereby dispersed over the surface of a heated Si(100) wafer. The chamber pressure was maintained at 5 Torr to 60 Torr during deposition. The growth rate of the silicon nitride films ranged from 20 Å/minute to 2 Å/minute depending upon pressure, temperature, NH$_3$ rate, and precursor rate.

Chemical analysis of the films, by a combination of RBS (Rutherford Backscattering), HFS (Hydrogen Forward Scattering), and NRA (Nuclear Reaction Analysis), and spectroscopic ellipsometry revealed that (NEt$_2$)$_2$(HNMe)Si—Si(HNMe)(NEt$_2$)$_2$ deposits films with increased the N/Si ratio along with higher ultra-violet absorption edge (UVAE) and index of refraction and decreased the impurity carbon and hydrogen content as shown in Table 2 below.

TABLE 2

Film composition for various deposition conditions
using the precursor (NEt$_2$)$_2$(HNMe)Si—Si(HNMe)(NEt$_2$)$_2$

| NH3 (sccm) | T (° C.) | P (torr) | Rate (Å/min) | n | UVAE (eV) | H (at %) | C (at %) | N/Si |
|---|---|---|---|---|---|---|---|---|
| 300 | 600 | 20 | 8 | 1.96 | 5.21 | 9.5 | 1.7 | 1.36 |
| 50 | 550 | 5 | 13 | 1.99 | 4.00 | 10.0 | 8.5 | 1.20 |

Example 6

Silicon Nitride Deposition with (HNBu$^t$)$_2$(HNMe)Si—Si(HNMe)(HNBu$^t$)$_2$

A solution of the compound of Example 2, (HNBu$^t$)$_2$(HNMe)Si—Si(HNMe)(HNBu$^t$)$_2$, was prepared at a concentration of 0.4M in a hydrocarbon solvent. This solution was metered at 0.0127 ml/minute or 0.025 ml/minute into a vaporizer that was held at temperature of 120° C. and had a flow of 10 standard cubic centimeters per minute (sccm) of He as a carrier gas. The vapor was mixed with 50 sccm or 300 sccm of NH$_3$ in a showerhead vaporizer device that was maintained at 120° C. and thereby dispersed over the surface of a heated Si(100) wafer. The chamber pressure was maintained at 20 Torr to 60 Torr during deposition. The growth rate of the silicon nitride films ranged from 30 Å/minute to 2 Å/minute depending upon pressure, temperature, NH$_3$ rate, and precursor rate.

Chemical analysis of the films, by a combination of RBS (Rutherford Backscattering), HFS (Hydrogen Forward Scattering), and NRA (Nuclear Reaction Analysis), and spectroscopic ellipsometry revealed that (HNBu$^t$)$_2$(HNMe)Si—Si(HNMe)(HNBu$^t$)$_2$ deposits films with super-stoichiometric N/Si ratio along with high ultra-violet absorption edge (UVAE) independent of process condition. Index of refraction and the impurity carbon and hydrogen contents were reduced as shown in Table 3 below.

TABLE 3

Film composition for various deposition conditions using
the precursor (HNBu$^t$)$_2$(HNMe)Si—Si(HNMe)(HNBu$^t$)$_2$

| NH3 (sccm) | T (° C.) | P (torr) | Rate (Å/min) | n | UVAE (eV) | H (at %) | C (at %) | N/Si |
|---|---|---|---|---|---|---|---|---|
| 50 | 550 | 20 | 13 | 1.83 | 5.14 | 12.5 | 6.9 | 1.47 |

Example 7

Silicon Nitride Deposition with (HNBu$^t$)$_2$(NH$_2$)Si—Si(NH$_2$)(HNBu$^t$)$_2$ A solution of the compound of Example 3, (HNBu$^t$)$_2$(NH$_2$)Si—Si(NH$_2$)(HNBu$^t$)$_2$, was prepared at a concentration of 0.4M in a hydrocarbon solvent and at a concentration of 0.072M in HN$^i$Pr$_2$. These solutions were metered at 0.0127 ml/minute or 0.025 ml/minute or 0.05 ml/minute or 0.07 ml/minute into a vaporizer that was held at temperature of 120° C. and had a flow of 10 standard cubic centimeters per minute (sccm) of He as a carrier gas. The vapor was mixed with 38 sccm to 300 sccm of NH$_3$ in a showerhead vaporizer device that was maintained at 120° C. and thereby dispersed over the surface of a heated Si(100) wafer. The chamber pressure was maintained at 4 Torr to 60 Torr during deposition. The growth rate of the silicon nitride films ranged from 68 Å/minute to 7 Å/minute depending upon pressure, temperature, NH$_3$ rate, and precursor rate.

Chemical analysis of the films, by a combination of RBS (Rutherford Backscattering), HFS (Hydrogen Forward Scattering), and NRA (Nuclear Reaction Analysis), and spectroscopic ellipsometry revealed that (HNBu$^t$)$_2$(NH$_2$)Si—Si(NH$_2$)(HNBu$^t$)$_2$ deposits films with high N/Si ratio along with high ultra-violet absorption edge (UVAE) independent of process condition. Index of refraction and the impurity carbon and hydrogen contents were reduced as shown in Table 4 below.

TABLE 4

Film composition for various deposition conditions
using the precursor (HNBu$^t$)$_2$(NH$_2$)Si—Si(NH$_2$)(HNBu$^t$)$_2$

| NH3 (sccm) | HN$^i$Pr$_2$ (sccm) | T (° C.) | P (torr) | Rate (Å/min) | n | UVAE (eV) | H (at %) | C (at %) | N/Si |
|---|---|---|---|---|---|---|---|---|---|
| 38 | 12 | 550 | 20 | 29 | 1.83 | 5.01 | 15.5 | 7.4 | 1.42 |
| 30 | 0 | 500 | 4 | 14 | 1.74 | 5.70 | 19.5 | 3.6 | 1.19 |

Example 8

Silicon Nitride Deposition with (HNBu$^t$)$_2$(NH$_2$)Si—Si(NH$_2$)(HNBu$^t$)$_2$ and (HNEt)$_3$Si—Si(HNEt)$_3$ A solution of two compounds: 0.0576M (HNBu$^t$)$_2$(NH$_2$)Si—Si(NH$_2$)(HNBu$^t$)$_2$, 0.0144M (HNEt)$_3$Si—Si(HNEt)$_3$ was prepared in HN$^i$Pr$_2$. This solution was metered at 0.0138 ml/minute into a vaporizer that was held at temperature of 120° C. and had a flow of 10 standard cubic centimeters per minute (sccm) of He as a carrier gas. The vapor was mixed with 275 sccm of NH$_3$ in a showerhead vaporizer device that was maintained at 120° C. and thereby dispersed over the surface of a heated Si(100) wafer. The chamber pressure was maintained at 10 Torr to 60 Torr during deposition. The growth rate of the silicon nitride films ranged from 33 Å/minute to 7 Å/minute depending upon pressure and temperature.

Chemical analysis of the films, by a combination of RBS (Rutherford Backscattering), HFS (Hydrogen Forward Scattering), and NRA (Nuclear Reaction Analysis), and spectroscopic ellipsometry revealed that the combination of (HNBu$^t$)$_2$(NH$_2$)Si—Si(NH$_2$)(HNBu$^t$)$_2$ with (HNEt)$_3$Si—Si(HNEt)$_3$ deposits films whose properties intermediate to those deposited from the two precursors independently Films with high N/Si ratio along with high ultra-violet absorption edge (UVAE), high index of refraction and very low impurity carbon and hydrogen contents were deposited as shown in Table 5 below.

TABLE 5

Film composition for various deposition conditions using the precursor
(HNBu$^r$)$_2$(NH$_2$)Si—Si(NH$_2$)(HNBu$^r$)$_2$ with (HNEt)$_3$Si—Si(HNEt)$_3$

| NH3 (sccm) | HN$^i$Pr$_2$ (sccm) | T (°C.) | P (torr) | Rate (Å/min) | n | UVAE (eV) | H (at %) | C (at %) | N/Si |
|---|---|---|---|---|---|---|---|---|---|
| 275 | 25 | 550 | 20 | 11 | 1.90 | 4.86 | 10.5 | 3.1 | 1.42 |

While the invention has been described herein with reference to various specific embodiments, it will be appreciated that the invention is not thus limited, and extends to and encompasses various other modifications and embodiments, as will be appreciated by those ordinarily skilled in the art. Accordingly, the invention is intended to be broadly construed and interpreted, in accordance with the ensuing claims.

What is claimed is:

1. A method of depositing a silicon-containing film on a substrate, comprising contacting the substrate with a composition comprising a disilane compound that is fully substituted with alkylamino (—NHR) and/or dialkylamino —N(R$_2$)) functional groups, wherein each R is independently selected from consisting of C$_{3-5}$ alkyl, under vapor deposition conditions.

2. The method of claim 1, wherein the silicon-containing film comprises a silicon nitride film.

3. The method of claim 1, wherein said vapor deposition conditions comprise temperature less than 300° C.

4. The method of claim 1, wherein the silicon-containing film comprises a low dielectric constant film.

5. The method of claim 1, wherein the silicon-containing film comprises a high k gate silicate film.

6. The method of claim 1, wherein said method is carried out to manufacture a semiconductor device.

7. The method of claim 1, wherein the disilane compound is fully substituted with alkylamino (—NHR) functional groups.

8. The method of claim 1, wherein the disilane compound is fully substituted with dialkylamino (—N(R$_2$)) functional groups.

* * * * *